United States Patent [19]
Karlin

[11] Patent Number: 6,062,855
[45] Date of Patent: May 16, 2000

[54] FRICTION-REDUCING ORTHODONTIC APPLIANCE

[76] Inventor: Jeffrey S. Karlin, 104 Cedar La., Apt. 5F, Teaneck, N.J. 07666

[21] Appl. No.: 09/296,811

[22] Filed: Apr. 23, 1999

Related U.S. Application Data

[60] Provisional application No. 60/088,935, Jun. 11, 1998.

[51] Int. Cl.[7] ........................................... A61C 3/00
[52] U.S. Cl. ........................................... 433/8; 433/20
[58] Field of Search ................... 433/8, 10, 18, 433/19, 24, 20, 189

[56] References Cited

U.S. PATENT DOCUMENTS

| | | | |
|---|---|---|---|
| 3,353,271 | 11/1967 | Blechman | 433/18 |
| 3,984,915 | 10/1976 | Noble et al. | 433/18 |
| 4,017,973 | 4/1977 | Nelson | 433/18 |
| 4,396,373 | 8/1983 | Dellinger | 433/19 |
| 4,424,030 | 1/1984 | Smiley et al. | 433/18 |
| 4,457,707 | 7/1984 | Smiley et al. | 433/18 |
| 4,508,505 | 4/1985 | Smiley et al. | 433/18 |
| 4,565,526 | 1/1986 | Kawata et al. | 433/8 |
| 4,595,361 | 6/1986 | Blechman et al. | 433/18 |
| 4,671,767 | 6/1987 | Blechman et al. | 433/19 |
| 4,802,849 | 2/1989 | Collins, Jr. | 433/19 |
| 5,205,736 | 4/1993 | Blechman | 433/18 |
| 5,277,581 | 1/1994 | Peterson | 433/5 |
| 5,334,015 | 8/1994 | Blechman | 433/18 |
| 5,607,299 | 3/1997 | Nicholson | 433/3 |

FOREIGN PATENT DOCUMENTS 0 563 685A1  10/1993  European Pat. Off. .

*Primary Examiner*—John J. Wilson
*Assistant Examiner*—Melba Bumgarner

[57] ABSTRACT

An orthodontic appliance in which friction is reduced between an archwire and its archwire holding element by means of repulsive forces. The repulsive forces are due to magnetic or electrical fields. The archwire holding element may be a tube, or a pair of tie wings and a slot. The archwire holding element generates a field having a sign. The archwire generates a field proximate to the archwire holding element having an identical sign. A repulsive force is therefore produced. The repulsive force minimizes contact between the archwire holding element and the archwire. This reduces frictional binding, which reduces the treatment time and/or the force necessary for successful orthodontic treatment.

12 Claims, 4 Drawing Sheets

FRICTION-REDUCING ORTHODONTIC APPLIANCE

CROSS-REFERENCE TO RELATED APPLICATION

This application claims the benefit of U.S. Provisional Patent Application Ser. No. 60/088,935, filed Jun. 11, 1998.

BACKGROUND OF THE INVENTION

1. Field of the Invention

The present invention relates generally to orthodontic appliances, and specifically to orthodontic appliances reducing friction between an archwire and its archwire holding element by means of repulsive forces due to magnetic or electrical fields.

2. Description of Related Art

Orthodontic appliances are used to correct irregularities or abnormalities in the teeth, particularly problems with misaligned or poorly spaced teeth. The goal is to create the proper bite of the teeth, proper spacing, and proper curvature of the mouth.

Braces attached to the teeth are the most common type of orthodontic appliance. Archwires fit into the braces and correct the position of each tooth by applying a corrective force. The corrective force gradually moves the tooth in the desired direction. The braces include metal, plastic, or ceramic brackets. The archwires fit into slots, tubes, or the like in the brackets. The archwires are metal wires made of nickel-titanium, stainless steel, or other alloys. The slots or tubes in the brackets are generally metal. The archwire is held in the bracket by a rubber band or other means, such as a metal cap attached to the bracket. The bracket is attached to the tooth or teeth by adhesive bonding or by a band. The archwires may slide along the bracket or tube, or the teeth may slide on the archwires. Repeated adjustments by a dentist or orthodontist are required to adjust the archwires and other components so that a force in the desired direction is produced.

A major problem with braces is frictional binding that occurs between the archwire and the bracket, slot, or tube. This frictional binding creates inefficient tooth movement. Frictional binding increases the amount of force that must be applied, since the friction requires force to overcome. If the amount of force applied does not change, frictional binding increases treatment time.

U.S. Pat. Nos. 3,353,271, 4,595,361, 4,671,767, 5,205,736, and 5,334,015 by Blechman disclose various types of orthodontic appliances through which corrective force is applied to teeth by magnets mounted on the teeth. Either attractive or repulsive magnetic force may be used. Blechman does not disclose the use of magnetized archwires, slots, tubes, or brackets. Blechman does not disclose the use of repellent magnetic forces to reduce friction in orthodontic appliances.

U.S. Pat. No. 3,984,915 by Noble discloses the orthodontic movement of teeth in the mouth using magnets directly bonded to the teeth to attract or repel adjacent magnets. Spacing can be corrected and twisted teeth can be torqued in a desired direction.

U.S. Pat. No. 5,607,299 by Nicholson discloses an orthodontic bracket having grooves to reduce friction between the bracket and an archwire.

None of the above inventions and patents, taken either singly or in combination, is seen to describe the instant invention as claimed.

SUMMARY OF THE INVENTION

The present invention is a friction-reducing orthodontic appliance. Friction is reduced between an archwire and its archwire holding element by means of repulsive forces due to electromagnetic fields.

Accordingly, it is a principal object of the invention to provide an orthodontic appliance which reduces frictional binding by means of repulsive forces acting between the archwire and its archwire holding element.

It is another object of the invention to provide an orthodontic appliance which uses repulsive forces between like magnetic poles or like electrical charges to reduce friction between an archwire and its archwire holding element.

It is a further object of the invention to provide an orthodontic appliance which reduces the force necessary for successful orthodontic treatment.

Still another object of the invention is to provide an orthodontic appliance which reduces the time needed for successful orthodontic treatment.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is a friction-reducing orthodontic appliance. Friction is reduced between an archwire and its archwire holding element by means of repulsive forces due to magnetic or electrical fields.

Figure 1:
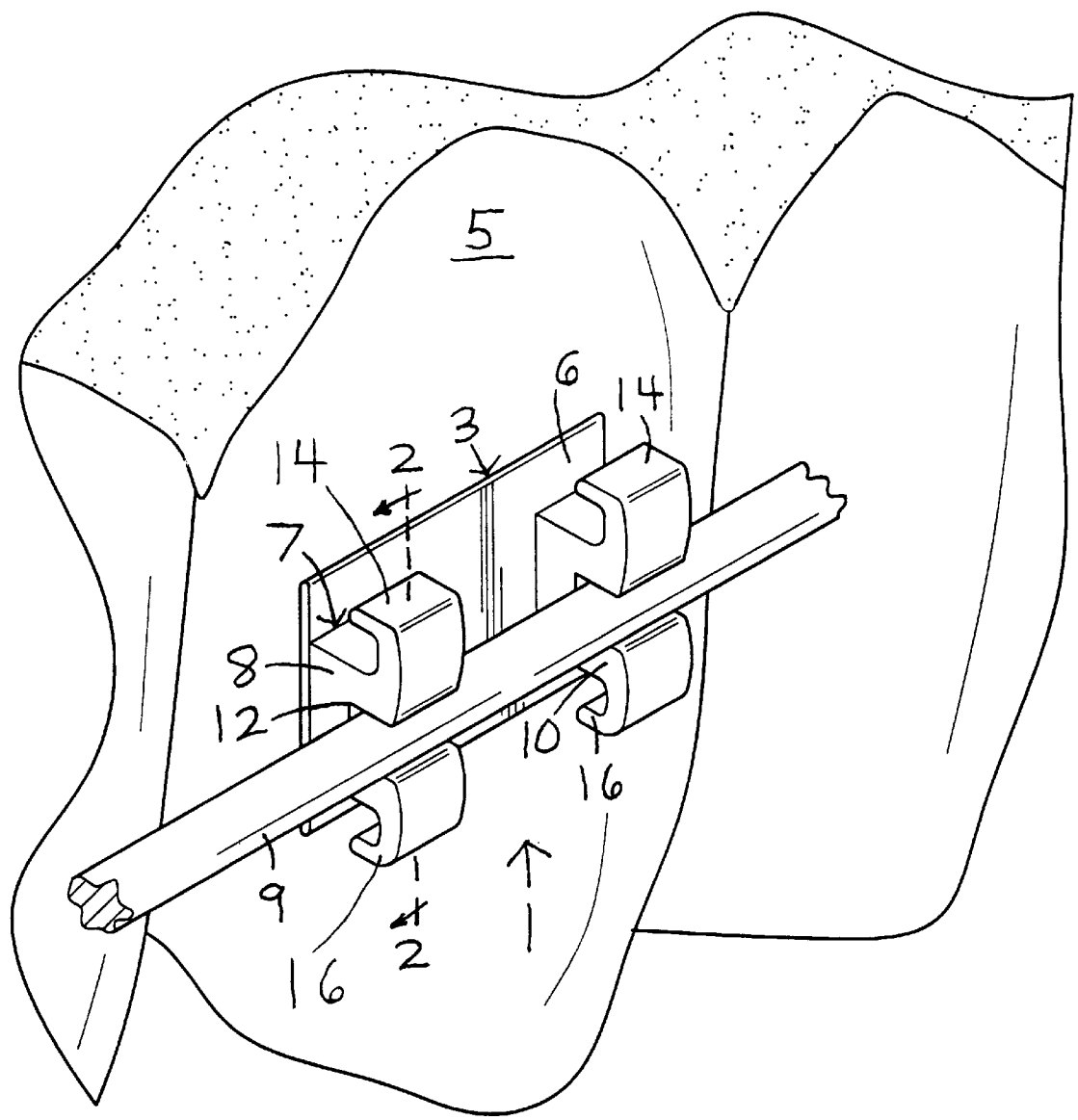
FIG. 1 is an environmental, perspective view of an orthodontic appliance according to the present invention, in which the repulsive forces are magnetic forces.

FIG. 1 is an environmental, perspective view of a first embodiment of a friction-reducing orthodontic appliance 1 according to the present invention. The orthodontic appliance 1 includes at least one bracket 3 adapted to be secured to a tooth 5 of a person. The bracket 3 is preferably directly bonded to the tooth 5. Bands may also be used, with the bracket 3 welded to the band. Only one bracket 3 is shown, but preferably each tooth has a bracket 3. The bracket shown is typical.

The bracket may vary in configuration. The bracket 3 ordinarily has a base plate 6 and an archwire holding element 7. The base plate 6 is planar. Typically the archwire holding element 7 includes two tie wings or tie arms 8 and 10 and a slot 12, as shown in FIG. 1. However, some brackets have no tie wings, while others have a single tie wing or three or more tie wings. In some brackets the archwire holding element is a gate or a tube. Each of the tie wings 8 and 10 in a typical bracket is generally U-shaped. Each tie wing 8 or 10 ordinarily has a pair of tie wing ears 14 and 16. The slot 12 is located between the tie wing ears 14 and 16.

The archwire holding element 7 generates a field within the archwire holding element 7. The field is an electromagnetic field. The field generated within the archwire holding element 7 has a sign. The sign may be either north or south (for a magnetic field) or positive or negative (for an electrical field).

The entire bracket may generate the field, if desired. Alternatively the base plate may be nonmagnetic and the field may be generated by only the archwire holding element, or by only a portion of the archwire holding element.

The orthodontic appliance 1 includes at least one archwire 9. Only a portion of the archwire 9 is shown, but the portion shown is typical of the remainder. The archwire has an elongated shape and is partially located within the archwire holding element. In a typical archwire holding element, the archwire lies in the slot 12 of each bracket. The archwire 9 is secured within the archwire holding element 7 by a standard archwire securing means. The securing means has been omitted from the figures for clarity. The securing means may be a ligature wire tied between the pair of tie wing ears 14 and 16 of the tie wing 10 and over the archwire 9. Other possible securing means include elastic ligatures, metal caps, and metal bracket gates.

The archwire 9 generates a field proximate to the archwire holding element 7. The field generated by the archwire 9 has a sign identical to the sign of the field generated by the archwire holding element 7. The result is that a repulsive force is produced between the holding element 7 and the archwire 9. The repulsive force reduces friction between the holding element 7 and the archwire 9.

The archwire 9 may be composed of a variety of materials. Possibilities include titanium, stainless steel, nickel, chromium, cobalt, aluminum, and other metals and alloys. The archwire preferably is composed of a permanently magnetized material.

Figure 2:
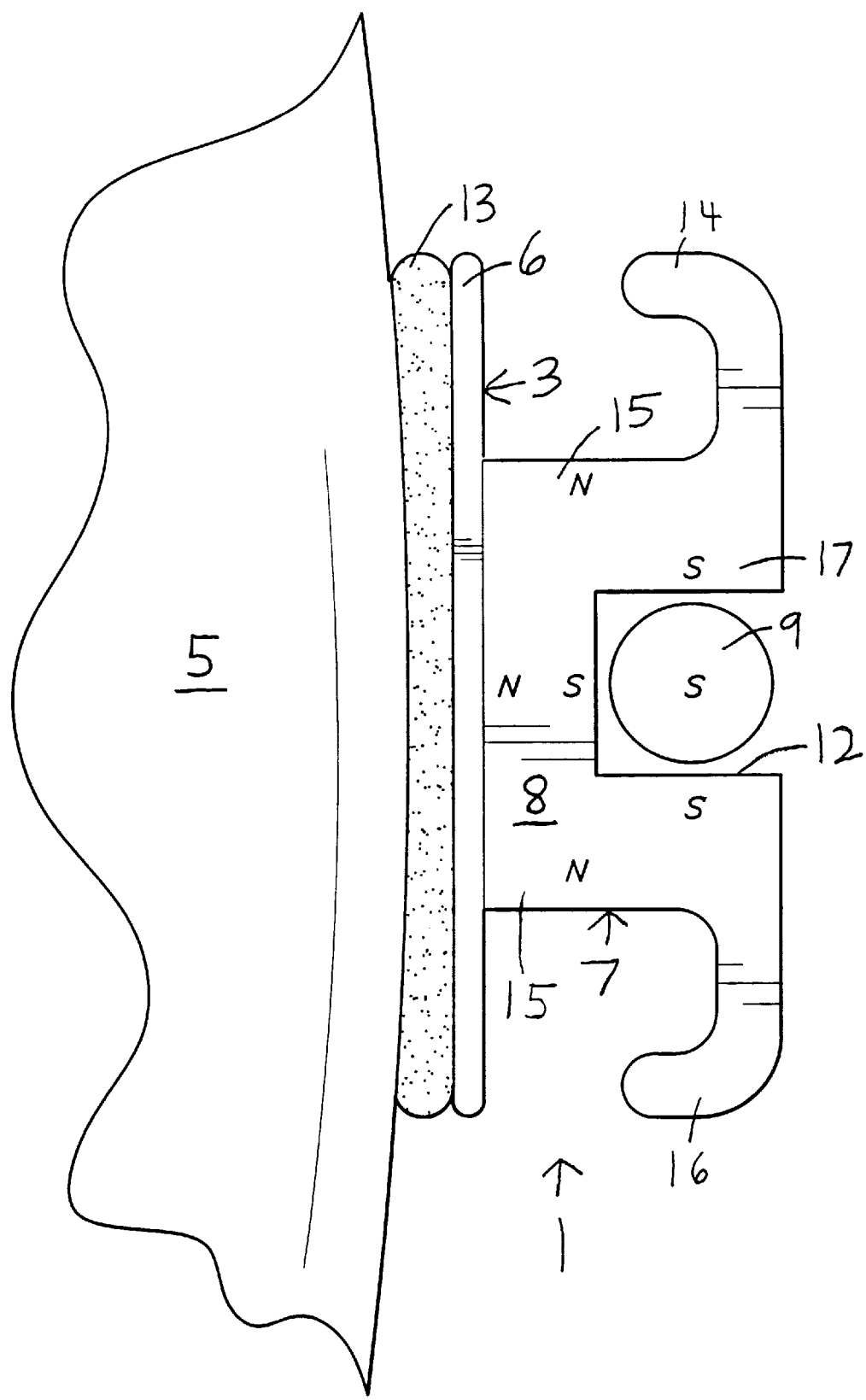
FIG. 2 is a sectional, side view drawn along line 2—2 of FIG. 1.

FIG. 2 is a sectional, side view drawn along line 2—2 of FIG. 1. The archwire holding element 7 may be composed of a variety of materials. Possibilities include metal, plastic, and ceramic, or a combination. A magnetized ceramic or ferrite may be used. Preferably the bracket 3 is a commercially available bracket modified as to its magnetic characteristics. The bracket 3 is bonded to the tooth 5 by an adhesive 13. In the orthodontic appliance 1 the fields generated by the archwire holding element 7 and the archwire 9 are magnetic fields. See FIG. 2. The repulsive force between them is a magnetic force. In the orthodontic appliance 1 the entire tie wing 8 is magnetically polarized. The tie wings 8 and 10 generate the magnetic field of the archwire holding element 7. The base plate 6 of the bracket 3 may or may not be polarized.

In the orthodontic appliance 1 the tie wings 8 and 10 have a direction of polarization. The tie wings 8 and 10 each have a tooth side 15 and an archwire side 17. The thickness dimension of the tie wings 8 and 10 extends from the tooth side 15 to the archwire side 17. The direction of polarization of the tie wings 8 and 10 is through the thickness dimension. The tooth side 15 is the north pole of the magnet, while the archwire side 17 is the south pole. A magnetic field is generated within the slot 12. Preferably all of the surfaces of the slot 12 contacting the archwire 9 would be magnetized. Magnetization of just one or two surfaces might be used where it is desirable, for economic or other reasons, to reduce friction on only some surfaces.

The archwire 9 may have various shapes and various directions of polarization. Any shape of archwire may be used, such as an archwire of rectangular or circular cross-section. Preferably the archwire 9 is a commercially available archwire modified as to its magnetic characteristics.

The archwire 9 of the orthodontic appliance 1 may be magnetically polarized along its length. At different points along the length of the archwire 9, the archwire will therefore have different polarization values. See FIGS. 2 and 3. For example, FIG. 2 shows the south pole of the archwire 9 located within the slot 12. Careful placement of the archwire 9 in relation to the bracket 3 is necessary for the signs of the magnetic fields to be identical. Generally two different types of brackets are required with opposite polarizations, for use at either end of the archwire.

Ideally, all of the brackets 3 are magnetized, and the archwire is strongly magnetized near all of the brackets 3. However, it is acceptable for only some of the brackets to be magnetized. For example, only two or three of the brackets may be magnetized at each side of the mouth. In this case, the archwire 9 might generate a magnetic field sufficiently strong to reduce friction over only ¼ of its length at each end. The brackets to be magnetized might be selected from those most likely to experience frictional binding with the archwire.

The magnetic repulsion between the poles minimizes contact between the archwire 9 and the bracket 3. Preferably there is no contact at all, and the archwire 9 magnetically levitates away from the surfaces of the slot 12. Since there is little or no contact, frictional binding between the archwire 9 and the bracket 3 is greatly reduced.

The reduced friction results in more efficient tooth movement, as friction does not have to be overcome. Less friction means that if the same force is applied, treatment time is decreased. The orthodontic appliance of the invention therefore reduces the treatment time necessary for successful orthodontic treatment. Alternatively, lighter forces may be used to make the same tooth movement without changing the treatment time. The orthodontic appliance of the invention reduces the force necessary for successful orthodontic treatment.

Figure 3:
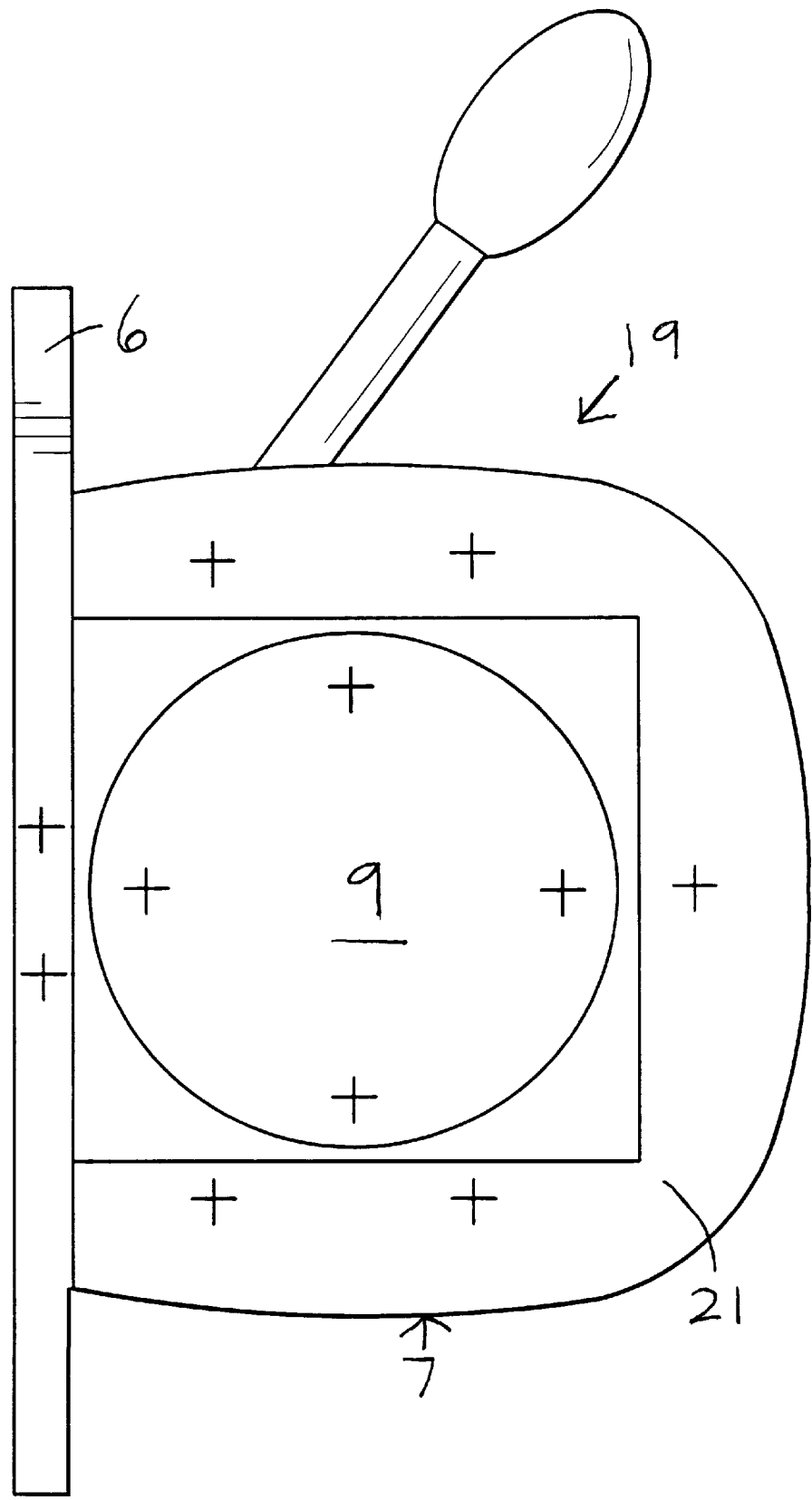
FIG. 3 is a side view of a second embodiment of the invention, in which the repulsive forces are provided by like electrical charges.

FIG. 3 is a side view of a second embodiment 19 of the invention. The archwire holding element 7 includes a tube 21. Tubes are frequently used as holding elements on molars. Magnetic repulsion may be used with tubes, just as in the first embodiment. Tubes have the advantage that the archwire can be surrounded by the magnetized tube, which equalizes the repulsive force acting on the archwire.

As shown in FIG. 3, in the orthodontic appliance 19 the tube 21 and the archwire 9 may have a positive electrical charge. The fields generated are therefore electrical fields. The archwire holding element 7 and the archwire 9 may be coated with an appropriate insulator to keep the charge from leaking away.

Figure 4:
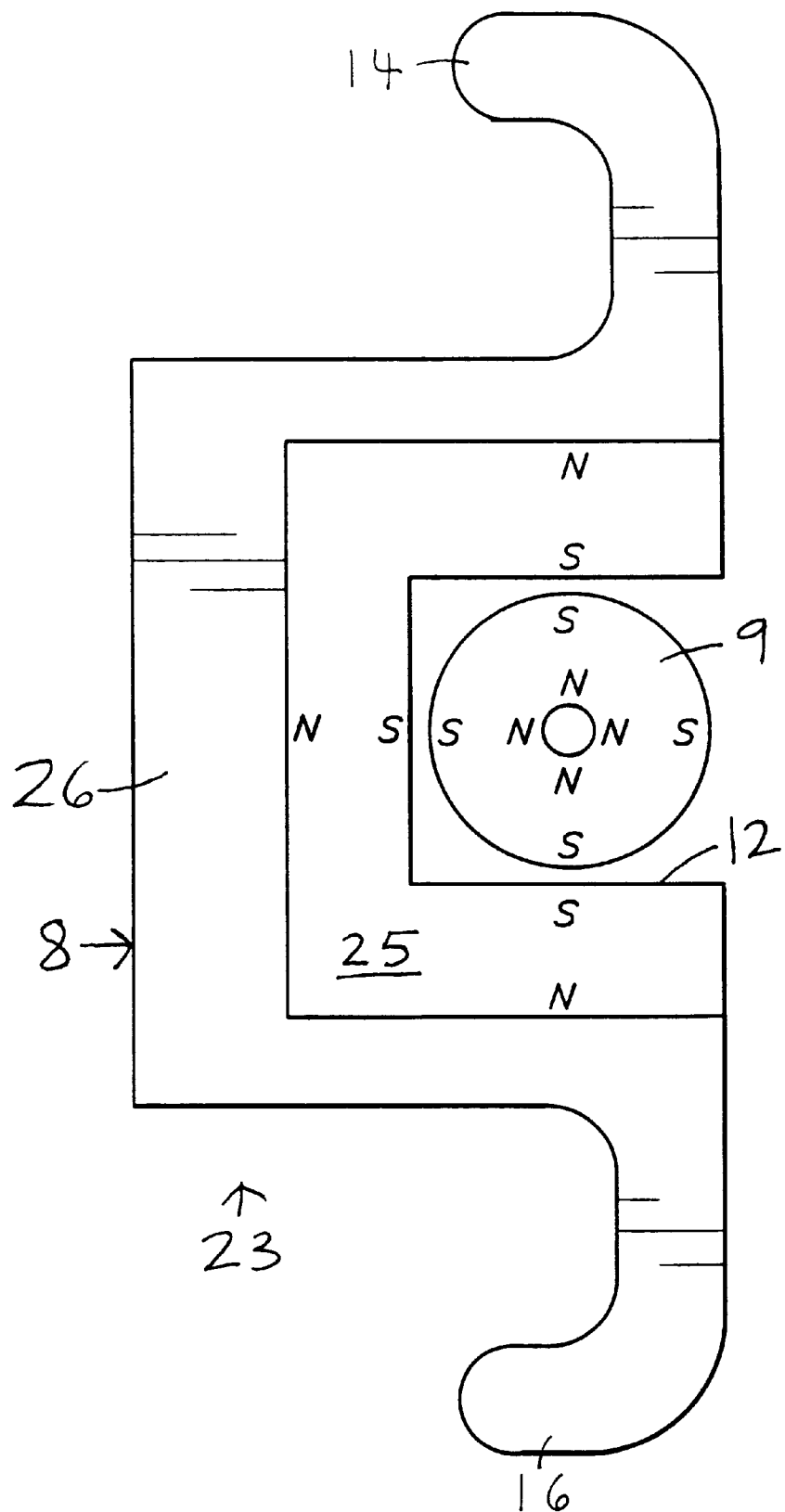
FIG. 4 is a side view of a third embodiment of the invention having a largely nonmagnetic bracket with the portion of the tie wing adjacent to the slot being magnetic.

FIG. 4 is a side view of a third embodiment 23 of the invention. Only the tie wing 8 is shown. The repulsive force is a magnetic force. Instead of the entire tie wing being magnetically polarized, as in the embodiment of FIG. 2, only a magnetic portion 25 of the tie wing 8 adjacent to the slot 12 generates the magnetic field. All the surfaces which might contact the archwire 9 are magnetized. The remainder of the tie wing 8 is nonmagnetic. For example, the nonmagnetic portion 26 of the tie wing 8 might be a non-ferromagnetic ceramic or plastic. The magnetic portion 25 of the tie wing 8 adjacent to the slot 12 might be composed of a permanently magnetic material, such as AlNiCo. The magnetic portion 25 is magnetically polarized through the thickness dimension.

Metal slots in ceramic brackets are commercially available, and would require modification only as to their magnetic characteristics. The magnetic portion 25 would be machined to the desired dimensions. The tie wing 8 would be made to incorporate the magnetic portion 25. The magnetic portion 25 might be attached by an adhesive or other means.

The archwire 9 of the orthodontic appliance 23 may be tubular, as shown in FIG. 4. For example, the north pole of the archwire 9 may be on the inside of the tube. The south pole of the archwire 9 would then be on the outside of the tube, proximate to the magnetically polarized portion 25. The south pole of the magnetic portion 25 therefore repels the archwire. Since the polarity is uniform the archwire 9 has no tendency to twist. The polarity of the archwire 9 is uniform along its length. The bracket 3 does not have to be located in any particular place for the signs of the magnetic fields to be identical. This arrangement has the advantage that only one type of bracket is needed, rather than two types with opposite polarizations.

In another embodiment of the invention, a magnetic coating might be applied to a bracket slot, a tube, or an archwire.

It is to be understood that the present invention is not limited to the sole embodiments described above, but encompasses any and all embodiments within the scope of the following claims.

I claim:

1. An orthodontic appliance, comprising
   (a) at least one bracket adapted to be secured to a tooth of a person, the bracket having an archwire holding element, the archwire holding element generating a field within the archwire holding element, the field having a sign; and
   (b) at least one archwire partially located within the archwire holding element, the archwire generating a field proximate to the archwire holding element, the field generated by the archwire having a sign identical to the sign of the field generated by the archwire holding element, so that a repulsive force is produced between the archwire holding element and the archwire, the repulsive force reducing friction between the holding element and the archwire.

2. An orthodontic appliance according to claim 1, wherein the archwire holding element is composed of at least one material selected from the group consisting of metal, plastic, and ceramic.

3. An orthodontic appliance according to claim 1, wherein the fields generated by the archwire holding element and the archwire are magnetic fields, and the repulsive force is a magnetic force.

4. An orthodontic appliance according to claim 1, wherein the fields generated by the archwire holding element and the archwire are electrical fields.

5. An orthodontic appliance according to claim 1, wherein the archwire has a circular cross-section.

6. An orthodontic appliance according to claim 1, wherein the archwire is tubular.

7. An orthodontic appliance according to claim 1, wherein the archwire holding element includes a tube, and the archwire is partially located within the tube.

8. An orthodontic appliance according to claim 1, wherein the archwire holding element includes at least one tie wing.

9. An orthodontic appliance according to claim 1, wherein the archwire holding element includes at least two tie wings.

10. An orthodontic appliance according to claim 1, wherein the fields generated by the archwire holding element and the archwire are magnetic fields, the repulsive force is a magnetic force, the archwire holding element includes at least one tie wing, the tie wing generates the magnetic field of the archwire holding element, the tie wing has a direction of polarization, a tooth side, an archwire side, and a thickness dimension extending from the tooth side to the archwire side, and the direction of polarization of the tie wing is through the thickness dimension.

11. An orthodontic appliance according to claim 1, wherein the archwire holding element includes at least one slot, and the archwire lies in the slot.

12. An orthodontic appliance according to claim 11, wherein the fields generated by the archwire holding element and the archwire are magnetic fields, the repulsive force is a magnetic force, the archwire holding element includes at least one tie wing, the tie wing has a magnetic portion and a nonmagnetic portion, and the magnetic portion of the tie wing is located adjacent to the slot and generates the magnetic field.

* * * * *